US009802839B2

(12) United States Patent
Wang et al.

(10) Patent No.: US 9,802,839 B2
(45) Date of Patent: Oct. 31, 2017

(54) METHOD OF PRODUCING POLYANILINE ZIRCONIA NANOCOMPOSITE AND USES THEREOF

(71) Applicant: Chung Yuan Christian University, Jhongli, Taoyuan County (TW)

(72) Inventors: Ya-Fen Wang, Zhubei (TW); Cheng-Hsien Tsai, Kaohsiung (TW); Chih-Sheng Tsai, Tainan (TW)

(73) Assignee: Chung Yuan Christian University, Johngli, Taoyuan County (TW)

( * ) Notice: Subject to any disclaimer, the term of this patent is extended or adjusted under 35 U.S.C. 154(b) by 259 days.

(21) Appl. No.: 14/593,732

(22) Filed: Jan. 9, 2015

(65) Prior Publication Data

US 2016/0198717 A1    Jul. 14, 2016

(51) Int. Cl.
| | | |
|---|---|---|
| *A01N 55/02* | (2006.01) |
| *C02F 1/28* | (2006.01) |
| *B01J 20/26* | (2006.01) |
| *B01J 20/06* | (2006.01) |
| *B01J 20/28* | (2006.01) |
| *B01J 20/30* | (2006.01) |
| *C02F 1/50* | (2006.01) |
| *A01N 25/10* | (2006.01) |
| *A01N 25/12* | (2006.01) |
| *A01N 59/16* | (2006.01) |
| *C02F 101/10* | (2006.01) |

(52) U.S. Cl.
CPC .............. *C02F 1/285* (2013.01); *A01N 25/10* (2013.01); *A01N 25/12* (2013.01); *A01N 55/02* (2013.01); *A01N 59/16* (2013.01); *B01J 20/06* (2013.01); *B01J 20/262* (2013.01); *B01J 20/28016* (2013.01); *B01J 20/3085* (2013.01); *C02F 1/281* (2013.01); *C02F 1/288* (2013.01); *C02F 1/50* (2013.01); *C02F 2101/105* (2013.01); *C02F 2303/04* (2013.01)

(58) Field of Classification Search
CPC combination set(s) only.
See application file for complete search history.

(56) References Cited

U.S. PATENT DOCUMENTS

2008/0287323 A1* 11/2008 Li ............................ C12N 9/99
                                                          507/211

* cited by examiner

*Primary Examiner* — Erma Cameron
(74) *Attorney, Agent, or Firm* — Muncy, Geissler, Olds & Lowe, P.C.

(57) ABSTRACT

Disclosed herein is a method of producing a polyaniline zirconia nanocomposite, and the uses of the thus produced polyaniline zirconia nanocomposite for the treatment of wastewater. The polyaniline zirconia nanocomposite is characterized in having a particle size of about 0.3 to 50 μm in diameter, an isoelectric point at about pH 6.2, and is capable of reducing at least 99% of the pathological microorganism and at least 60% of the phosphate in the wastewater after coming into contact with wastewater for 24 hrs and 12 hrs, respectively.

8 Claims, 6 Drawing Sheets

METHOD OF PRODUCING POLYANILINE ZIRCONIA NANOCOMPOSITE AND USES THEREOF

BACKGROUND OF THE INVENTION

1. Field of the Invention

The present disclosure concerns in general, the production of a polyaniline zirconia nanocomposite, and its use for the treatment of wastewater.

2. Description of Related Art

Many processes and systems for wastewater treatment are known in the prior art. Preliminary wastewater treatment usually involves gravity sedimentation of screened wastewater to remove settled solids. Half of the solids suspended in wastewater are removed through primary treatment. Secondary wastewater treatment is usually accomplished through a biological process, removing biodegradable material. Tertiary or advanced treatment is used when extremely high-quality effluent is required, including direct discharge to a drinking water source. Typical tertiary treatment involves use of chlorine for the reduction of pathological microorganisms (e.g., *E. coli*), which inevitably results in the use of additional chemicals (e.g., sodium thiosulfate) to remove chlorine post-treatment. Reclaiming the additional chemicals and/or brine content of the wastewater before discharge usually involves more expensive process, such as reverse osmosis and distillation, and ion exchange methods.

Accordingly, there exists in the related art a need for an economically efficient way to reduce the level of pathological microorganisms as well as the brine content in the wastewater.

SUMMARY

The present disclosure concerns in general, the production of a polyaniline zirconia nanocomposite, and its use for the treatment of wastewater.

In one aspect, the present disclosure provides a method for producing a polyaniline zirconia nanocomposite. The method includes steps of, (a) mixing zirconium and a cationic surfactant in water in the presence of a base to produce a gel mixture;

(b) allowing the gel mixture to age to produce a zirconia nanoparticle; and (d) mixing the zirconia nanoparticle of step (b) with aniline in water in the presence of an acid to produce the polyaniline zirconia nanocomposite.

According to preferred embodiments, the polyaniline zirconia nanocomposite has a particle size of about 0.3 to 50 μm in diameter; and can reach the isoelectric point at approximately pH 6.2.

In step (a), the cationic surfactant may be any of cetyl trimethylammonium bromide (CTAB), cetyl pyridinium chloride or polyethoexylated tallow amin (POEA). Preferably, the cationic surfactant is CTAB.

According to preferred embodiments, the zirconium and the cationic surfactant are mixed in a ratio of about 2:1 by weight.

According to certain embodiments, in the step (a), the base is ammonia; and in step (c), the acid is hydrochloride.

According to certain embodiments, in the step (b), the gel mixture is aged for at least 24 hrs.

According to certain embodiments, in the step (c), the zirconia nanoparticle of the step (b) and the aniline are mixed in a ratio of about 1:3 by weight.

According to optional embodiments, the method further includes the step of, adding an initiator in the step (c) to initiate the polymerization of aniline. In some examples, the initiator is ammonium persulfate (APS).

In another aspect, the present disclosure provides a method for treating a wastewater. The method includes steps of, subjecting the wastewater to the treatment of the polyaniline zirconia nanocomposite produced by the method of the present disclosure for a sufficient period of time, so as to reduce the respective levels of a pathological microorganism and a phosphate in the wastewater.

According to preferred embodiments, the polyaniline zirconia nanocomposite has a particle size of about 0.3 to 50 μm in diameter; and reaches an isoelectric point at approximately pH 6.2.

According to certain embodiments, the pathological microorganism is *Staphylococcus aureus* or *Escherichia coli*.

According to certain embodiments, at least 95% of the pathological microorganism in the wastewater is eradicated after 24 hrs; preferably, at least 99% of the pathological microorganism in the wastewater is eradicated after being treated for 24 hrs.

According to certain embodiments, at least 60% of the phosphate in the wastewater is removed after being treated for 12 hrs.

The details of one or more embodiments of the invention are set forth in the accompanying description below. Other features and advantages of the invention will be apparent from the detail descriptions, and from claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present description will be better understood from the following detailed description read in light of the accompanying drawings, where.

DESCRIPTION

Figure 1:
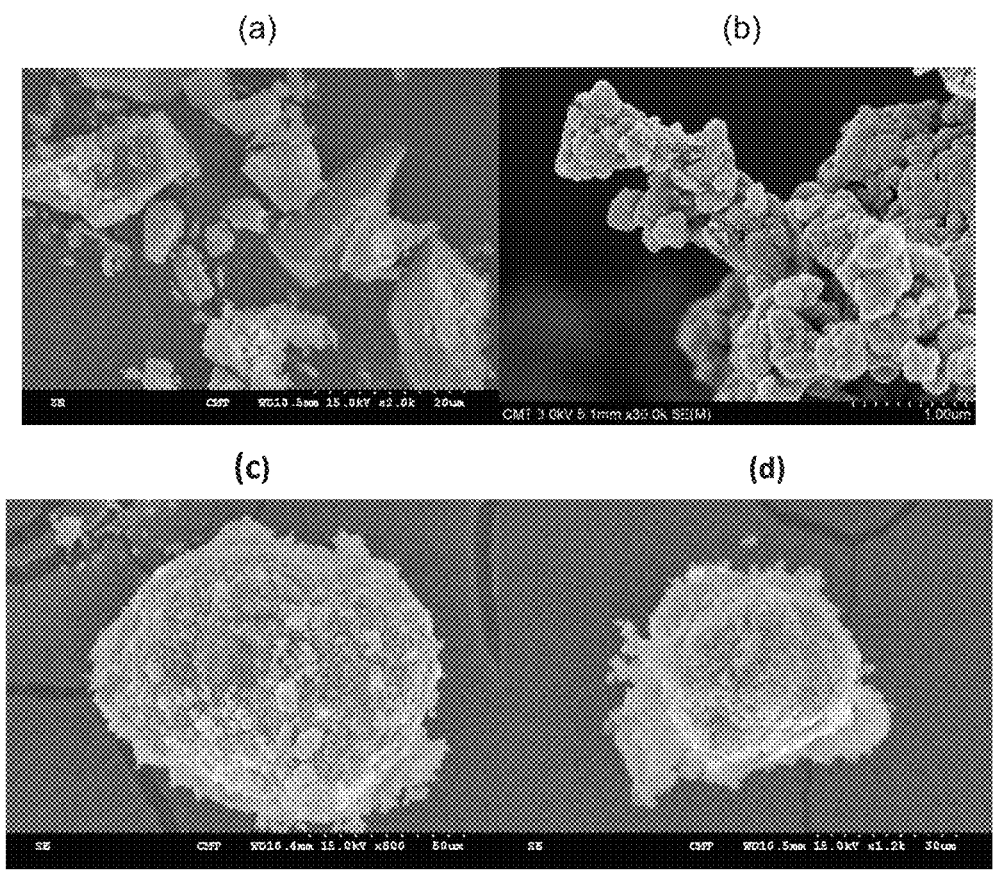
FIG. 1 are SEM photographs of (a) zirconia nanoparticles of example 1.1, (b) polyaniline of example 1.2, the polyaniline zirconia nanocomposite of example 1.3 respectively at the magnification of (c) 800 folds, and (d) 1200 folds, in accordance with one embodiment of the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

The singular forms "a", "and", and "the" are used herein to include plural referents unless the context clearly dictates otherwise.

In the first aspect, the present disclosure entails a modified sol-gel process for producing a polyaniline zirconia nanocomposite, which possesses unique anti-microbial and phosphate adsorption properties. Accordingly, the polyaniline zirconia nanocomposite produced by the present method is a value tool for applications in which reduction of bacterial counts and phosphate levels are sought. In particular, the polyaniline zirconia nanocomposite produced by the present method finds utilities in the treatment of wastewater.

It is therefore the first objective of the present disclosure to provide a method of producing a polyaniline zirconia nanocomposite. Specifically, the polyaniline zirconia nanocomposite of the present invention is produced from a modified sol-gel process, which comprises steps of, (a) mixing zirconium and a cationic surfactant in water in the presence of a base to produce a gel mixture;

(b) allowing the gel mixture to age to produce a zirconia nanoparticle; and (c) mixing the zirconia nanoparticle of the step (b) with aniline in water in the presence of an acid, so as to produce the polyaniline zirconia nanocomposite.

A sol-gel process in general involves first the formation of a sol, which is a suspension of solid particles in a liquid, then of a gel, which is a diphasic material with a solid encapsulating a liquid. The liquid can then be removed from the gel by drying and/or heat treatment.

Accordingly, in the step (a) of the present method, zirconium and a cationic surfactant are mixed in a ratio of about 5:1 to 1:5 by weight, such as 5:1, 4:1, 3:1, 2:1, 1:1, 1:2, 1:3, 1:4 and 1:5 by weight; preferably, in a ratio of about 2:1 by weight, in water to form a gel mixture. Examples of cationic surfactants useful in the present disclosure include, but are not limited to, cetyl trimethylammonium bromide (CTAB), eetyl pyridinium chloride and polyethoxylated tallow amine (POEA). Preferably, the cationic surfactant is CTAB. Further, the gel formation process of step (a) needs to take place in the presence of a base, preferably a weak base, such as methyl amine, pyridine, and ammonia. In one preferred example, zirconium and CTAB are mixed in a ratio of about 2:1 by weight in water containing ammonia.

The thus formed gel is then let stand for at least 12 hrs, such as 12, 14, 16, 18, 20, 22, 24, 26, 28 and 30 hours, before subjecting it to drying and/or heat treatment, to remove the solvent (i.e., water) therein. According to preferred embodiment, in the step (b) of the present method, the thus formed gel in step (a) is let stand for 24 hrs, to produce a zirconia nanoparticle.

To generate the desired polyaniline zirconia nanocomposite, in which the zirconia nanoparticle of the step (b) is encapsulated or enclosed by polyaniline, accordingly in the step (c), the zirconia nanoparticle of step (b) is mixed with aniline monomer in a ratio of about 5:1 to 1:5 by weight, such as 5:1, 4:1, 3:1, 2:1, 1:1, 1:2, 1:3, 1:4 and 1:5 by weight, in water in the presence of an acid. Preferably, in the step (c), the zirconia nanoparticle of the step (b) is mixed with aniline in a ratio of about 1:3 by weight in water. Further, the step (c) needs to take place in the presence of an acid, preferably a strong acid, such as nitric acid, sulfuric acid, and hydrogen chloride.

According to optional embodiments, the method may further include the step of, adding an initiator in the step (c) to initiate the polymerization of aniline. In some examples, the initiator is ammonium persulfate (APS). Alternatively, other suitable initiator may be used, as long as it help initiating the polymerization of aniline.

Subsequently, the product of the step (c) is further subjected to a drying process, so as to remove any residual solvent therein and generate the desired polyaniline zirconia nanocomposite.

In some optional embodiments, the respective products of the steps (b) and (c) are filtered before being subject to subsequent treatments.

According to preferred embodiments, the polyaniline zirconia nanocomposite thus produced has a particle size of about 0.3-50 μm in diameter, such as 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50 μm in diameter; preferably about 5 to 45 μm in diameter, such as 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45 μm in diameter; and more preferably about 15 to 40 μm in diameter, such as 15, 16, 17, 18, 19, 20, 21, 22, 23, 24, 25, 26, 27, 28, 29, 30, 31, 32, 33, 34, 35, 36, 37, 38, 39, 40 μm in diameter; and can reach the isoelectric point at approximately pH 6.2.

The second aspect of the present disclosure is to provide a method of treating a wastewater. The method comprises steps of, subjecting the wastewater to the treatment of the polyaniline zirconia nanocomposite produced by the present method for a sufficient period of time, so as to reduce the respective levels of a pathological microorganism and a phosphate in the wastewater.

According to preferred embodiments, the polyaniline zirconia nanocomposite produced by the method of the present disclosure has a particle size of about 40 μm in diameter; and reaches the isoelectric point at approximately pH 6.2.

According to certain embodiments, the wastewater is allowed to contact the polyaniline zirconia nanocomposite produced by the present method for at least 12 hrs, such as 12, 14, 16, 18, 20, 22, 24, 26, 28 and 30 hrs so as to reduce the respective levels of the pathological microorganism and the phosphate therein. Preferably, the wastewater is allowed to be in contact with polyaniline zirconia nanocomposite produced by the present method for at least 20 hrs, such as 20, 22, 24, 26, 28 and 30 hrs; more preferably, for at least 24 hrs, such as 24, 26, 28 and 30 hrs.

According to certain embodiments, the growth of the pathological microorganism that may be suppress or inhibit by the polyaniline zirconia nanocomposite produced by the present method is *Staphylococcus aureus* or *Escherichia coli*.

According to certain embodiments, at least 95% of the pathological microorganism in the wastewater is eradicated after 24 hrs; preferably, at least 99% of the pathological microorganism in the wastewater is eradicated after being treated for 24 hrs.

According to certain embodiments, at least 60% of the phosphate in the wastewater is removed after being treated for 12 hrs.

The present invention will now be described more specifically with reference to the following embodiments, which are provided for the purpose of demonstration rather than limitation.

Examples

Materials and Methods

X-Ray Powder Diffractometry.

X-ray diffraction patterns were obtained on D2 phaser X-ray diffractometer system (Bruker AXS Gmbh, Germany). Samples were scanned in continuous mode from 5-50° (2θ) with step size of 5θ/min on a spinning stage at 30 kV and 10 mA with Cu Kα radiation. The incident beam path was equipped with a 1 mm divergence slit and 1 mm air scattering screen. The diffracted beam was equipped with Ni-filter. Detection was accomplished with a Lynxeye (2.5) detector (Bruker AXS).

Scanning Electron Microscopy (SEM)

SEM was performed on ground materials by an electron microscope JEOL Model JSM-6390LV at various magnifications (5× to 300,000×).

Zeta Potential Measurement

Zeta potential is a measure of the magnitude of the electrostatic or charge repulsion/attraction between particles, and is one of the fundamental parameters known to affect stability. Measurement of zeta potential was performed on the polyaniline zirconia nanocomposite by Zetasizer 3000 (Malvern, USA).

Agar Well Diffusion Method

Zirconia (0.05 g) and polyaniline zirconia nanocomposite (0.1 g) were respectively mixed with acetone to form homogeneous solutions. Paper discs were then coated with the thus formed zirconia or polyaniline zirconia nanocomposite solution, and air dried at 60° C. The coated paper discs were then placed on top of agar plates previously inoculated with $10^5$ to $10^6$ CFU/mL of $E.$ $Coli$ or $S.$ $aureus$. The plates were subsequently incubated at 37° C. for 48 hrs, and the area of inhibition was determined by measuring the paper area (in mm) where no sign of bacteria growth was found. The measured diameter of the inhibition zone was then compared with that of the control.

Preparation of Zirconia, Polyaniline, or Polyaniline Zirconia Nanocomposite Coated Iron Substrate Zirconia, polyaniline, and polyaniline zirconia nanocomposite (1 g) were respectively mixed with acetone (10 mL) to form suspensions, then MP45 epoxy resin (1 g) was added therein to each suspensions, and continued to stir each suspensions for 1 hr to ensure thorough mixing. For coating purpose, an iron substrate (3 cm×9 cm) was repeatedly immersed into the suspension for several times, then air dried at 60° C.

Minimum Inhibitory Concentration (MIC)

MIC was determined using a standardized test method termed JIS Z 2801, which is a test designed to quantitatively test the ability of an antimicrobial surface to inhibit the growth of microorganisms or kill them, over a 24 hour period of contact.

Standard dilutions of $10^1$-$10^8$ CFU/mL of $E.$ $Coli$ or $S.$ $aureus$ were performed, and their respective absorbance at 600 nm were measured. 100 μL of a solution containing 10 CFU/mL $E.$ $Coli$ or $S.$ $aureus$ was applied onto the surface of a microscope glass slide pre-coated with various concentrations of zirconia, polyaniline, or polyaniline zirconia nanocomposite, then covered with a piece of plastic cover (about 1 cm×1 cm) to ensure the bacterial were fully in contact with the microscope glass slide surface. The entire microscope glass slide was then placed in 10 mL NaCl solution and in a shaker and shook for 10 min. 1 mL of such solution was then taken out and mixed with Tryptic Soy Agar (TPS), and subsequently applied onto the surface of an agar plate. The agar plate was then incubated at 37° C. for 48 hrs, and the number of survived bacterial present on the agar plate was enumerated and a percent and $\log_{10}$ reduction was determined for the treated test material as compared to the untreated control material.

Minimum Bactericidal concentration (MBC)

MBC is the lowest concentration of any antibiotic or antibacterial agent, in which 99.9% of the original inoculated bacteria is killed. Zirconia, polyaniline, or polyaniline zirconia nanocomposite (0.001 g/mL or 0.002 g/mL) was added to a bacterial solution containing $10^6$ CFU/mL of $E.$ $Coli$ or $S.$ $aureus$, the bacteria count was then determined at various time points, including 0, 2, 6, 12 and 24 hrs. At each designated time interval, 1 mL of the bacterial solution was taken out and mixed with TSA, then spread on the surface of an agar plate. The plate was then incubated at 37° C. for 48 hrs, the number of bacterial present on the agar plate was then determined.

Phosphate Adsorption Analysis

A phosphate solution (200 mg/L, 450 mL) was mixed with 600 mg Zirconia, polyaniline, or polyaniline zirconia nanocomposite and let stand for at least 24 hrs. An aliquot of the solution was taken out at various designated time points, such as 0, 0.5, 1, 2, 6, 12 and 24 hrs, and filtered through a 0.45 μm membrane filter, the filtrate was then subjected to phosphate analysis.

To determine the concentration of phosphate in the filtrate, 0.4 g of ammonium persulfate (APS) was added into 50 mL of the filtrate, and the mixture was autoclaved for 30 min so as to prevent further growth of any bacterial therein. The absorbance of the mixture at 880 nm was then measured, and the phosphate concentration of the mixture was then determined by interpolating from a standard absorbance curve obtained by use of various known concentrations of phosphate samples.

Example 1 Preparation and Characterization of Polyaniline Zirconia Nanocomposite)

1.1 Preparation of Zirconia Nanoparticles by Sol-Gel Method

In a flask, mixed $ZrOCl.8H_2O$ (0.61 g, purchased from ACROS organics), cetyl trimethylammonium bromide (CTAB) (0.3 g) and water (80 mL), and continuously stirred the mixture until it was homogeneous, then 1.5 mL ammonium was added. Continued to stir the mixture for another 24 hrs, at which time, alcohol started to appear above the mixture, and was subsequently removed by decantation. The remaining solution was centrifuged at a speed of 8,500 rpm for 5 minutes to give a white precipitate, which was dried in an oven at 60° C. for 1 hr.

1.2 Preparation of Polyaniline

In a flask, mixed aniline (4 mL) and deionized water (400 mL), then added HCl solution (12 M, 20 mL) in a drop-wise manner. The mixture was stirred continuously until it cooled to the room temperature, then 1.5 mL ammonium persulfate (APS) was added. Continued to stir the mixture for another 18 hrs, then washed with acetone. The product was collected by filtering, and was further dried at 60° C.

1.3 Preparation of Polyaniline Zirconia Nanocomposite

In a flask, mixed the zirconia nanoparticles of example 1.1 (0.3 g), aniline (4 mL), and deionized water (400 mL), HCl solution (12 M, 20 mL) was then added in a drop-wise manner and added persulfate (APS, 2.6 g). Continuously stirred the mixture for 12 hrs. The resulting mixture was then washed, and filtered to produce polyaniline zirconia nanocomposite (1 g).

Example 2 Characterization of the Polyaniline Zirconia Nanocomposite of Example 1.3

2.1 SEM and Powder X-Ray Diffraction Pattern

FIG. 1 are SEM photographs of (a) zirconia nanoparticles of example 1.1, (b) polyaniline of example 1.2, the polyaniline zirconia nanocomposite of example 1.3 respectively at the magnification of (c) 800 folds, and (d) 1,200 folds. The zirconia nanoparticles of example 1.1 appeared to possess a crystalline morphology, whereas the polyaniline of example 1.2 is amorphous. As to the polyaniline zirconia nanocomposite of example 1.3, it appears to be spherical in shape, in which the zirconia nanoparticles are incorporated into the matrix of polyaniline.

The size analysis indicated that the zirconia nanoparticle of example 1.1, polyaniline of example 1.2, and the polyaniline zirconia nanocomposite of example 1.3 are respectively about 1.08-6.15 μm, 857 nm to 1.39 μm, and 45.3 μm in diameter.

Figure 2:
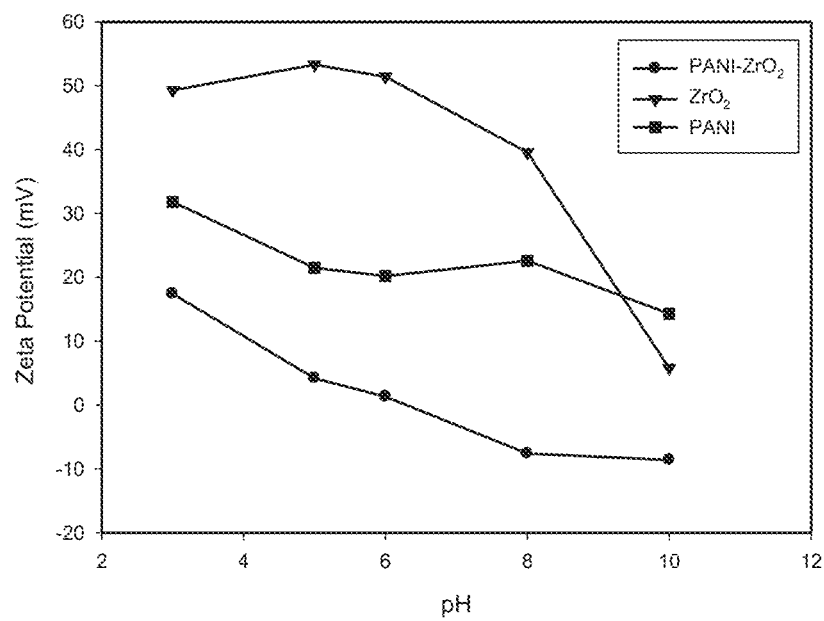
FIG. 2 is a line graph illustrating the respective zeta potentials of the zirconia nanoparticles of example 1.1, the polyaniline of example 1.2, and the polyaniline zirconia nanocomposite of example 1.3 at various pH levels in accordance with one embodiment of the present disclosure.

FIG. 2 illustrates zeta potential analysis of zirconia nanoparticles of example 1.1, the polyaniline of example 1.2, and the polyaniline zirconia nanocomposite of example 1.3. It appears that the polyaniline zirconia nanocomposite of example 1.3 carries positive charges at pH 3-6, with an isoelectric point at approximate pH 6.2. As to polyaniline and zirconia nanoparticle of examples 1.1 and 1.2, they both possess high zeta potential and therefore would be highly stable in both acid and alkaline conditions.

Figure 3:
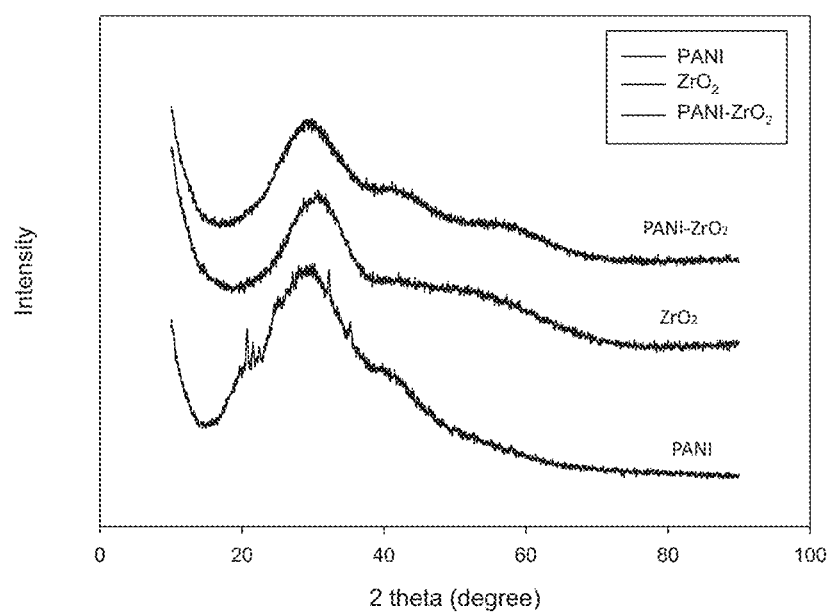
FIG. 3 illustrates the respective powder X-ray diffraction patterns of the zirconia nanoparticles of example 1.1, the polyaniline of example 1.2, and the polyaniline zirconia nanocomposite of example 1.3 in accordance with one embodiment of the present disclosure.

The X-ray diffraction patterns of the zirconia nanoparticle of example 1.1, the polyaniline of example 1.2, and the polyaniline zirconia nanocomposite of example 1.3 are respectively illustrated in FIG. 3. A significant broad diffraction peak was observed at approximately 23.44° at reflection angle 28 for the polyaniline of example 1.2, whereas no significant diffraction peaks were observed for the polyaniline zirconia nanocomposite of example 1.3, possibly due to insignificant amount of zirconia nanoparticles incorporated therein.

2.2 Antibacterial Activity

The antibacterial activity of the zirconia nanoparticle of example 1.1, the polyaniline of example 1.2 or the polyaniline zirconia nanocomposite of example 1.3 was investigated by use of agar well diffusion method, as well as the measurements of minimum inhibitory concentration (MIC) and minimum bactericidal concentration (MBC).

The agar well diffusion method is a simple test useful for verifying whether a test agent is bactericidal. Specifically, paper discs pre-impregnated with a test antibiotic (e.g., the polyaniline zirconia nanocomposite of example 1.3) are placed on top of an agar plate pre-inoculated with a pathological microorganism (e.g., S. aureus or E. Coli), and the agar plate is then left incubated. If the test agent killed the pathological microorganism, there will be an area on the agar plate where the growth of the pathological microorganism is not visible to the naked eyes, and the size of this area depends on how effective the test agent is at stopping the growth of the pathological microorganism. A stronger antibiotic will create a larger zone, because a lower concentration of the antibiotic is enough to stop growth. In this example, a zone of 20 mm represents significant antibactericidal activity, 10-12 mm represents good anti-bactericidal activity, 7-9 mm represents low anti-bactericidal activity, whereas a zone smaller than 7 mm represents anti-bactericidal activity that is un-significant. Results are summarized in Table 1.

TABLE 1

Growth inhibition zone in mm
Growth Inhibition Zone (mm)

| test agent | E. Coli | S. aureus |
|---|---|---|
| the zircornia nanoparticle of example 1.1 | | |
| 0.001 g/mL | 12 ± 0.7 | 15 ± 0.57 |
| 0.002 g/mL | 19 ± 0.67 | 22 ± 0.28 |
| the polyaniline of example 1.2 | | |
| 0.001 g/mL | 7 ± 0.17 | 8 ± 0.23 |
| 0.002 g/mL | 9 ± 0.57 | 10 ± 0.15 |
| the polyaniline zircornia nanocomposite of example 1.3 | | |
| 0.001 g/mL | 11 ± 0.32 | 15 ± 0.25 |
| 0.002 g/mL | 14 ± 0.7 | 18 ± 0.21 |

It is evident from results presented in table 1, the polyaniline of example 1.2 exhibited low anti-bactericidal activity toward either E. Coli or S. aureus; whereas both the zirconia nanoparticle of example 1.1 and the polyaniline zirconia nanocomposite of example 1.3 were effective in suppressing the growth of both E. Coli and S. aureus, and the inhibitory effect increased with an increase in the concentration of the test agent.

Similar to the concept of the agar well diffusion method, MIC and MBC methods were both employed to further evaluate the antibacterial activity of the zirconia nanoparticles of example 1.1 and the polyaniline zirconia nanocomposite of example 1.3 according to the procedures described in the "Materials and Methods" section. Briefly, MIC gives the lowest concentration of any antibiotic or antibacterial agent that inhibits visible growth of an inoculated bacteria after overnight incubation; whereas MBC gives the lowest concentration of any antibiotic or antibacterial agent, in which 99.9% of the original inoculated bacteria is killed. Results are respectively summarized in Table 2 and FIG. 4.

TABLE 2

MIC determined by JIS Z 2801
MIC

| test agent | E. Coli | S. aureus |
|---|---|---|
| the zircornia nanoparticle of example 1.1 | | |
| 0.001 g/mL | 3 | 2 |
| 0.002 g/mL | 0 | 0 |
| the polyaniline of example 1.2 | | |
| 0.001 g/mL | 20 | 15 |
| 0.002 g/mL | 0 | 0 |
| the polyaniline zircornia | | |

TABLE 2-continued

MIC determined by JIS Z 2801

| test agent | MIC | |
|---|---|---|
| | E. Coli | S. aureus |
| nanocomposite of example 1.3 | | |
| 0.001 g/mL | 17 | 9 |
| 0.002 g/mL | 0 | 0 |

According to Table 2, at a lower concentration of 0.001 g/mL, the polyaniline zirconia nanocomposite of example 1.3 exhibited a mild antibacterial activity toward both test microorganisms among the tree test agents, whereas at a higher concentration of 0.002 g/mL, all three agents were effective to the same extend.

Figure 4A:
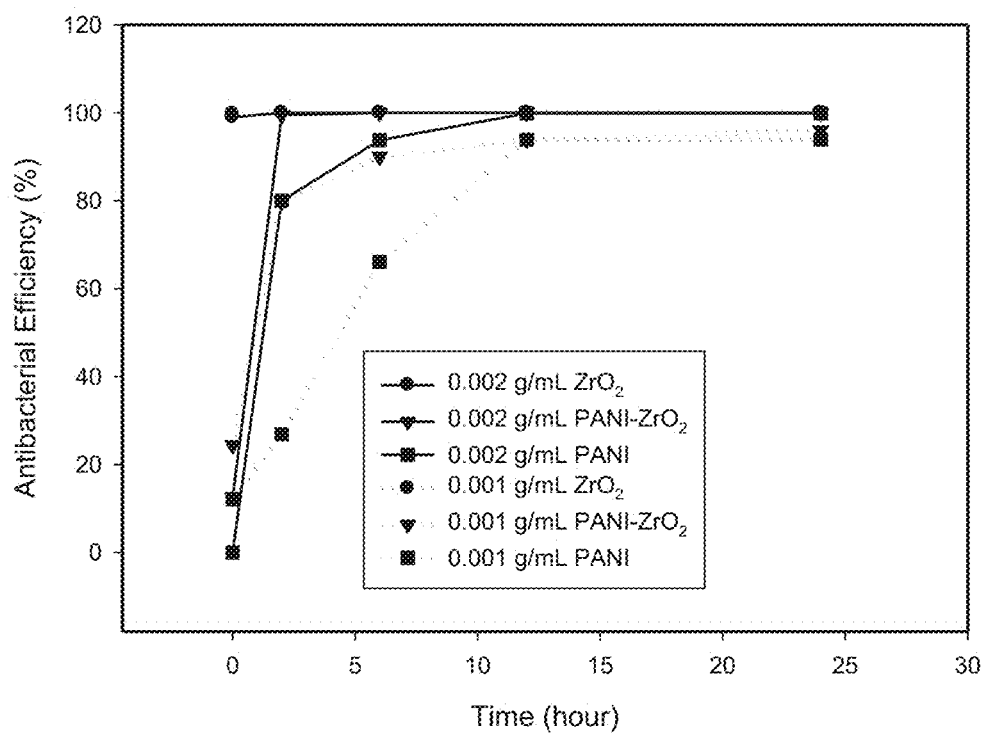
FIG. 4A illustrates the respective antibacterial efficacy of the zirconia nanoparticles of example 1.1, the polyaniline of example 1.2, and the polyaniline zirconia nanocomposite of example 1.3 toward *E. Coli* in accordance with one embodiment of the present disclosure.
Figure 4B:
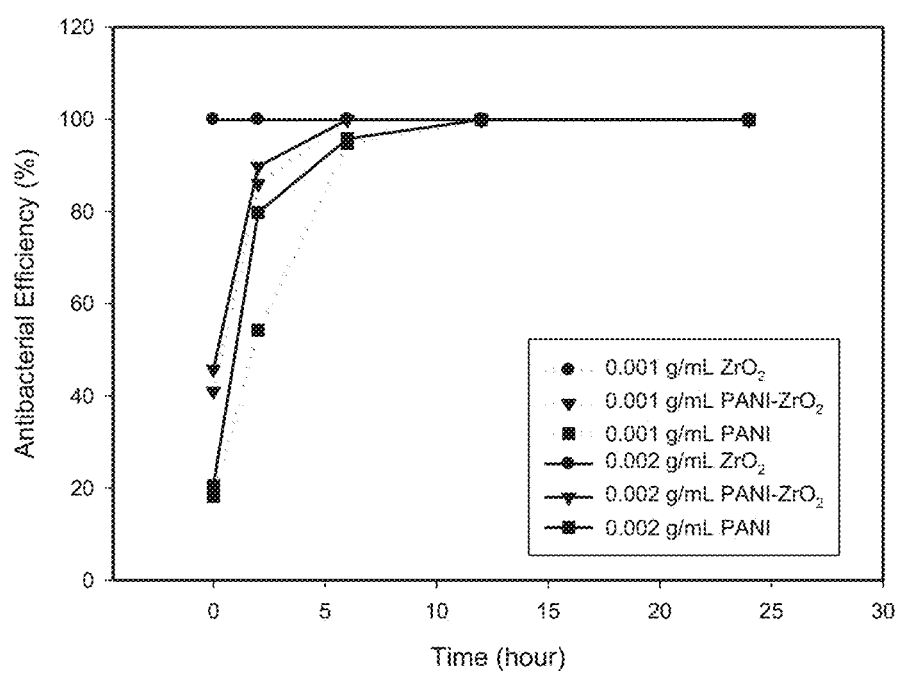
FIG. 4B illustrates the respective antibacterial efficacy of the zirconia nanoparticles of example 1.1, the polyaniline of example 1.2, and the polyaniline zirconia nanocomposite of example 1.3 toward *S. aureus* in accordance with one embodiment of the present disclosure.

The antibacterial efficacy of the test agents towards *E. Coli* and *S. aureus* measured by MBC method are respectively illustrated in FIG. 4A and FIG. 48B. As depicted in FIG. 4A, at the lower concentration of 0.001 g/mL, approximately 95% of *E. Coli* was killed after coming into contact with the polyaniline of example 1.2 or the polyaniline zirconia nanocomposite of example 1.3 for 24 hours; whereas over 99.99% of *E. Coli* was extinguished after contacting the zirconia nanoparticle of example 1.1. Further, at the concentration of 0.002 g/mL, over 99.99% of *E. Coli* was killed after coming into contact with any of the test agents for 12 hrs.

As to the antibacterial efficacy of the test agents toward *S. aureus*, at the concentration of 0.001 g/mL, over 99.9% of *S. aureus* was eradicated in 6 hrs by any of the zirconia nanoparticle of example 1.1, the polyaniline of example 1.2 or the polyaniline zirconia nanocomposite of example 1.3. When the concentration of the test agent was increased to 0.002 g/mL, over 99.99% of *S. aureus* was killed instantaneously by the zirconia nanoparticle of example 1.1, whereas over 99.9% of *S. aureus* was eradicated within 6 hrs by the polyaniline of example 1.2 and the polyaniline zirconia nanocomposite of example 1.3, respectively.

In sum, it is evident that both the polyaniline of example 1.2 and the polyaniline zirconia nanocomposite of example 1.3 are more effective in eradicating *S. aureus* than *E. Coli*, whereas the zirconia nanoparticle of example 1.1 remains to be the most potent anti-bactericidal agent among all.

2.3 Anti-Corrosion Activity

In this example, the capability of the zirconia nanoparticle of example 1.1, the polyaniline of example 1.2 or the polyaniline zirconia nanocomposite of example 1.3 in protecting the surface of an iron substrate was investigated.

The iron substrates coated with any of the test agents were prepared in according to procedures described in the "Materials and Methods" section, in which the zirconia nanoparticle of example 1.1 coated surface appeared to be white in color; whereas both the polyaniline-coated and the polyaniline zirconia nanocomposite coated surfaces appeared to be black. Corrosion tests were conducted by immersing any of the thus prepared substrates in 3.5% or 7.5% NaCl solutions for 1 month, in which a blank iron substrate was used as a control. Results are summarized in Table 3.

TABLE 3

Corrosion test using 3.5% and 7.5% NaCl solutions

| Sample | Corrosion Test | |
|---|---|---|
| | 3.5% NaCl | 7.5% NaCl |
| Blank iron substrate | rustic | Severe rust formation |
| Iron substrate coated with the zircornia nanoparticle of example 1.1 | Clear metallic surface | Clear metallic surface |
| Iron substrate coated with the polyaniline of example 1.2 | Rustic spots across the surface | rustic |
| Iron substrate coated with the polyaniline zircornia nanocomposite of example 1.3 | Clear metallic surface | Clear metallic surface |

2.4 Phosphate Adsorption

In this example, iron substrates pre-coated with the zirconia nanoparticle of example 1.1, the polyaniline of example 1.2 or the polyaniline zirconia nanocomposite of example 1.3 were allowed to come into contact with phosphate solutions for various periods of time, the remaining amounts of the phosphates in the solutions were then determined. Results are depicted in FIG. 5.

Figure 5:
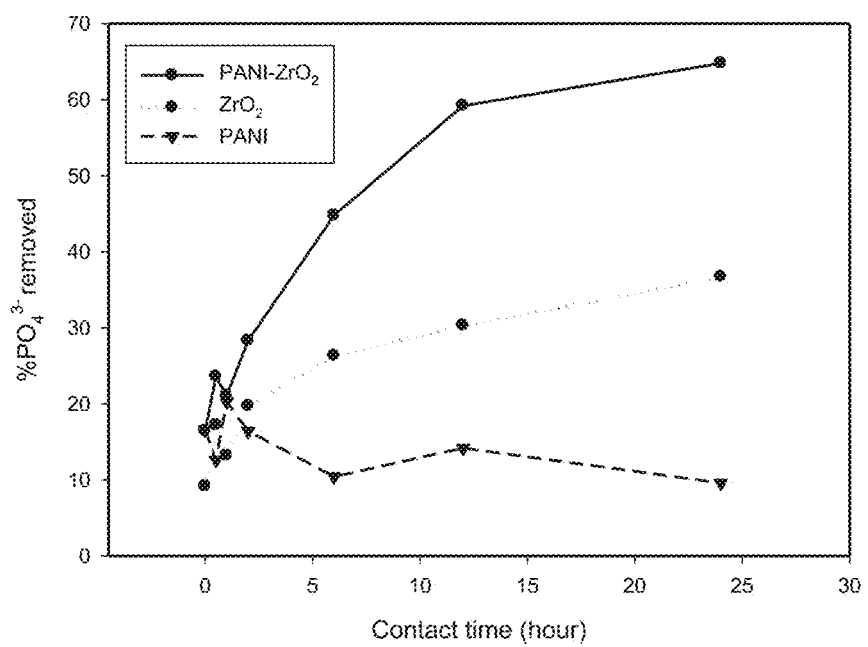
FIG. 5 illustrates the respective phosphate removal abilities of the zirconia nanoparticles of example 1.1, the polyaniline of example 1.2, and the polyaniline zirconia nanocomposite of example 1.3 in accordance with one embodiment of the present disclosure.

As depicted in FIG. 5, the polyaniline zirconia nanocomposite of example 1.4 was most effective in removing phosphate from the phosphate sample, with at least 60% phosphate being removed after 24 hrs; while about 37% and 10% phosphate removal were observed for the zirconia nanoparticle of example 1.1 and the polyaniline of example 1.2, respectively.

Taken together from the data above, the polyaniline zirconia nanocomposite of the present application is a potential material for various applications such as an additive of a paint or a material for water treatment, in which anti-corrosion, anti-bacterial, as well as phosphate removal properties are sought.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for producing a polyaniline zirconia nanocomposite comprising steps of,
   (a) mixing a compound comprising zirconium and a cationic surfactant in water in the presence of a base to produce a gel mixture;
   (b) allowing the gel mixture to age for at least 12 hours to produce a zirconia nanoparticle; and
   (c) mixing the zirconia nanoparticle of the step (b) with aniline in water in the presence of an acid so as to produce the polyaniline zirconia nanocomposite.

2. The method of claim 1, wherein the polyaniline zirconia nanocomposite has a particle size of about 0.3 to 50 μm in diameter; and reaches an isoelectric point at approximately pH 6.2.

3. The method of claim 1, wherein the cationic surfactant is cetyl trimethylammonium bromide (CTAB), cetyl pyridinium chloride or polyethoxylated tallow amine (POEA).

4. The method of claim 3, wherein in the step (a), the compound comprising zirconium and CTAB are mixed in a ratio of about 2:1 by weight.

5. The method of claim 1, wherein in the step (a), the base is ammonia; and in the step (c), the acid is hydrochloride.

6. The method of claim 1, wherein in the step (c), the product of the step (b) and the aniline is mixed in a ratio of 1:3 by weight.

7. The method of claim 6, further comprising adding an initiator in the step (c) to initiate the polymerization of aniline.

8. The method of claim 7, wherein the initiator is ammonium persulfate (APS).

* * * * *